US 6,508,831 B1

(12) United States Patent
Kushnir (10) Patent No.: US 6,508,831 B1
(45) Date of Patent: Jan. 21, 2003

(54) SYSTEM AND METHOD FOR HEAT CONTROL OF A LIVING BODY

(75) Inventor: Igal Kushnir, Pardes Chana (IL)

(73) Assignee: M.T.R.E. Advanced Technology Ltd., Caesaria (IL)

( * ) Notice: Subject to any disclaimer, the term of this patent is extended or adjusted under 35 U.S.C. 154(b) by 0 days.

(21) Appl. No.: 09/623,423

(22) PCT Filed: Jan. 29, 1999

(86) PCT No.: PCT/IL99/00059
§ 371 (c)(1),
(2), (4) Date: Oct. 11, 2000

(87) PCT Pub. No.: WO99/44552
PCT Pub. Date: Sep. 10, 1999

(30) Foreign Application Priority Data

Mar. 5, 1998 (IL) ................................................ 123573
Oct. 27, 1998 (IL) ................................................ 126783

(51) Int. Cl.⁷ .................................................. A61F 7/00
(52) U.S. Cl. ........................................ 607/104; 165/46
(58) Field of Search ................................ 607/104, 108; 165/46

(56) References Cited

U.S. PATENT DOCUMENTS

| 3,507,321 A | * | 4/1970 | Palma .......................... 165/46 |
| 3,738,367 A | | 6/1973 | Hardy |
| 4,094,357 A | | 6/1978 | Sgroi |
| 4,094,367 A | | 6/1978 | Jones et al. |
| 4,149,541 A | | 4/1979 | Gammons et al. |
| 4,691,762 A | | 9/1987 | Elkins, et al. |
| 4,807,447 A | | 2/1989 | Macdonald et al. |
| 4,844,072 A | | 7/1989 | French et al. |
| 5,097,829 A | | 3/1992 | Quisenberry |
| 5,184,612 A | | 2/1993 | Augustine |
| 5,269,369 A | | 12/1993 | Faghri |
| 5,383,918 A | * | 1/1995 | Panetta ........................ 607/104 |
| 5,411,541 A | | 5/1995 | Bell, et al. |
| 5,415,618 A | * | 5/1995 | Koch ........................... 600/22 |
| 5,609,619 A | | 3/1997 | Pompei |

(List continued on next page.)

FOREIGN PATENT DOCUMENTS

| GB | 2 263 872 | 8/1993 |
| WO | 96/26693 | 9/1996 |

OTHER PUBLICATIONS

Mallinckrodt, Inc., company web site, www.mallinckrodt.com/respiratory/productcatalog/product.asp?id=94, CareQulit Pediatric Warming Blanket, product of Mallinckrodt, Inc., 2000.

(List continued on next page.)

Primary Examiner—John Fox
(74) Attorney, Agent, or Firm—Nath & Associates PLLC; Gary M. Nath; Todd L. Juneau (57) ABSTRACT

A system and method for controlling an individual's body and temperature are provided. The system comprises a heat exchanger for transferring heat to or removing heat from portions of the individual's body surface, at least one BCT-sensing device for measuring the individual's actual BCT (aBCT) and emitting an aBCT data signal, at least one sensing device for measuring a parameter indicative of the heat transfer dynamics (HTD) between the body surface and the body's core, and emitting an HTD data signal, and a control module for receiving data signal from measuring devices, comprising the aBCT data signal and the HTD data signal, and for emitting a control signal for controlling heat exchange properties of the heat exchanger as a function of the data signals and a desired body core temperature (dBCT).

34 Claims, 8 Drawing Sheets

U.S. PATENT DOCUMENTS

| | | | | |
|---|---|---|---|---|
| 5,683,438 A | * | 11/1997 | Grahn | 607/104 |
| 5,913,886 A | * | 6/1999 | Soloman | 607/108 |
| 6,109,338 A | * | 8/2000 | Butzer | 165/46 |
| 6,119,474 A | * | 9/2000 | Augustine et al. | 62/259.3 |
| 6,143,020 A | * | 11/2000 | Shigezawa et al. | 607/96 |
| 6,149,674 A | * | 11/2000 | Borders | 607/96 |
| 6,197,045 B1 | * | 3/2001 | Carson | 607/104 |
| 6,209,144 B1 | * | 4/2001 | Carter | 2/458 |

OTHER PUBLICATIONS

Mallinckrodt, Inc., company web site, www.mallinckrodt.com/respiratory/productcatalog/product.asp?id=99, Model 5200 Warming Unit, product of Mallinckrodt, Inc., 2000.

Mallinckrodt, Inc., company web site, www.mallinckrodt.com/respiratory/productcatalog/product.asp?id=164 Warm-flo FW538 Fluid Warmer, product of Mallinckrodt, Inc., 2000.

Mallinckrodt, Inc., company web site, www.mallinckrodt.com/respiratory/productcatalog/product.asp?id=140 Warm-flo FW537 Fluid Warmer, product of Mallinckrodt, Inc., 2000.

Mallinckrodt, Inc., company web site, www.mallinckrodt.com/respiratory/productcatalog/product.asp?id=141 Warm-flo Blood & IV Sets and Accessories, product of Mallinckrodt, Inc., 2000.

Mallinckrodt, Inc., company web site www.mallinckrodt.com/respiratory/productcatalog/product.asp?id=143 Warm-flo Irrigation Pump, product of Mallinckrodt, Inc., 2000.

Mallinckrodt, Inc., company web site www.mallinckrodt.com/respiratory/productcatalog/product.asp?id=142 Warm-flo Pressure Infusor, product of Mallinckrodt, Inc., 2000.

Mallinckrodt, Inc., company web site, www.mallinckrodt.com/respiratory/resp/index.html Respiratory Home Page for products of Mallinckrodt, Inc., 2000.

Mallinckrodt, Inc., company web site, www.mallinckrodt.com/respiratory/productcatalog/results.asp?by=category&category=28&category2=&category 3=3, Product Line of temperature Probes and Monitors of Mallinckrodt, Inc., 2000.

Mallinckrodt, Inc., company web site, www.mallinckrodt.com/respiratory/productcatalog/product.asp?id=96, Care-Drape Upper Body Warming Blanket, product of Mallinckrodt, Inc., 2000.

Mallinckrodt, Inc., company web site, www.mallinckrodt.com/respiratory/productcatalog/product.asp?id=97, Care-Drape Lower Body Warming Blanket, product of Mallinckrodt, Inc., 2000.

Mallinckrodt, Inc., company web site, www.mallinckrodt.com/respiratory/productcatalog/product.asp?id=98, Care-Drape Pediatric Warming Blanket, product of Mallinckrodt, Inc., 2000.

Mallinckrodt, Inc., company web site, www.mallinckrodt.com/respiratory/productcatalog/product.asp?id=95, CareQuilt Full–Body/Multi–Access Warming Blanket, product of Mallinckrodt, Inc., 2000.

* cited by examiner

SYSTEM AND METHOD FOR HEAT CONTROL OF A LIVING BODY

FIELD OF THE INVENTION

The present invention concerns a system and method for thermoregulations of a living body. The system and method of the invention may be applied to both humans and animals.

BACKGROUND OF THE INVENTION AND PRIOR ART

A living body can maintain a normal body temperature, which in humans is about 36.5–37° C., under normal conditions. However, when subjected to extreme temperature conditions or to a variety of medical treatments, the body may not be able to properly regulate the body temperature. This is the case, for example: in individuals exposed to extreme temperatures; and in a variety of physiological disorders and medical conditions (e.g. general anesthesia) where the body loses its ability to properly regulate the body temperature.

Hypothermia is a reduction in body temperature which may result from exposure to a cold environment. Mild hypothermia in which body's core temperature (namely the temperature of internal organs and tissue within the body) is reduced by about 2° C. below the normal temperature, commonly occurs during and following surgery that is conducted under general anesthesia, as patients tend to lose body heat due to lowered metabolism and as a result of exposure of internal body organs or tissue, e.g. in an abdominal or thoracic cavity, to ambient air.

Hypothermia is experienced by more than 60% of patients after surgery. and in some surgical procedures, e.g. open heart surgery, hypothermia is experienced by more than 90% of adult patients.

Hypothermia can cause various severe physiological problems including cardiac morbidity, coagulopathy, impaired immune function, impaired wound healing, shivering, altered pharmaconnected properties of drugs, etc.

Hyperthermia, namely increase in body temperature above normal levels, may also cause various physiological disorders and if extreme, may be life threatening.

The clinical need to provide means for body temperature control has long been recognized.

MicroClimate Systems Inc., Stanford, Mich., U.S.A. markets a series of portable personal cooling systems (sold under the trademarks KOOLVEST, KOOLJACKET, KOOLBAND, KOOLPAID and others) which are intended for use by healthy persons who perform a physical activity in a hot environment (see Internet http://www.microclimate.com/prodline.html or http://www.microclimate.com/work.html). The system consists of a garment (it may be a vest, jacket, skull cap, a cervical collar, etc.) with tubing embedded therein in which water flows propelled by a battery-powered pump. Water passes through ice or through a cooling device before entering the tubing within the garment. The user can control the pump rate, the temperature, etc. A similar product line is also provided by Mallinckrodt Inc., St. Louis, Mo., U.S.A. (see the Internet at http://www/mallinckrodt.com/ccd) and others.

A similar system is disclosed in U.S. Pat. No. 4,807,447 (Macdonald et al). The unique feature of this system is that the person's breathing is used to operate the refrigerant compressor.

Various systems making use of garments, pads or blankets with heat transfer elements, e.g. conduits embedded therein, are disclosed in U.S. Pat. Nos. 3,738,367, 4,094,357, 4,094, 367, 4,149,541, 4,844,072, 5,184,612 and 5,269,369. However, due to various physiological reasons, realized only in accordance with the present invention and which will be specified further below, none of the above systems provides adequate control of body temperature of the individuals in general, and of patients following surgery before undertaking general anesthesia in particular.

There is also a need for control of body temperature in veterinary medicine, particularly the control of body temperature during surgery under general anesthesia. Animals, and particularly small animals, occasionally die following surgery, owing to uncontrolled changes in body temperature.

GENERAL DESCRIPTION OF THE INVENTION

In the following, the term "core temperature" will be used to denote the temperature within the body, namely that of the internal organs and tissue. Core temperature is typically measured through the rectum ("rectal temperature measurement") but may also he measured by inserting probes through a variety of other body cavities, e.g. mouth, nasal or ear temperature probes. The term "surface temperature" will be used to denote the temperature of the external body surface, (which may be that of the skin or, where the skin has been removed, e.g. in a bun injury, that of the most external layers). It should be noted that surface temperature may vary between different body portions. The surface temperature may be measured by a variety of temperature probes including, for example, an infrared sensor measuring infrared emission from a specific skin portion, probes attached to the skin such as a thermo-couple devices, thermistor, etc.

In accordance with the present invention, it has been realized that a major deficiency of prior art thermoregulatory devices is that these do not sufficiently reconcile the fact that the body is not a passive heat conductor but rather employs intrinsic dynamic physiological thermoregulation mechanisms which can change the heat transfer properties between the body's core and the periphery. For example, when exposed to a low temperature, there is a vasoconstriction of peripheral blood vessels, thus reducing blood flow to the periphery and thereby reducing heat transfer between the periphery and the body's core. In other situations there is vasodilatation resulting in increased blood flow to the periphery above normal levels thus bringing an increase in heat transfer rate between the body's core and the periphery.

In accordance with the invention, a system and method for the control of body temperature is provided. The system and method of the invention allows controlled cooling of body temperature, controlled heating, as well as regulating an individual's body temperature to remain at a desired set temperature. It is a unique feature of the invention that it takes into consideration the complexity of the heat transfer regiment from the skin to the body's core. This complexity is manifested by dynamic heat transfer properties, namely physiological changes which can alter the rate in which heat can be transferred between the skin and the body's core. Such heat transfer dynamics (HTD) may be determined by a variety of means, as will be illustrated further below.

In accordance with the invention there is provided a system for controlling an individual's body core temperature (BCT) comprising:

a heat exchanger for transferring heat to or removing heat from portions of the individual's body surface;

at least one BCT-sensing device for measuring the individual's actual BCT (aBCT) and emitting an aBCT data signal;

at least one sensing device for measuring a parameter indicative of the heat transfer dynamics (HTD) between the body surface and the body's core, and emitting an HTD data signal; and a control module for receiving data signals from measuring devices. comprising the aBCT data signal and the HTD data signal, and for emitting a control signal for controlling heat exchange properties of said heat exchanger as a function of the data signals and the desired body core temperature (dBCT).

The heat exchange may either be provided with an internal heat or cold producing capability, e.g. including a Peltier effects modules, or the heat exchanger may be linked to at least one source of cold and/or hot fluid, which fluid then circulates between such source and the heat exchanges to transfer heat/cold between the exchanger and said source.

By another aspect, the present invention provides a method for controlling internal body temperature of an individual, comprising the following steps:

(a) defining a desired body core temperature (dBCT);

(b) providing a heat exchanger and bringing it into contact with at least a portion of the individual's external body surface, for heat transfer to or heat removal from the body portion;

(c) continuously measuring parameters including at least the actual body core temperature (aBCT) and a parameter indicative of the heat transfer dynamics (HTD) between the body's surface and the body' core; and (d) in a processor, receiving data signals corresponding with the measured parameters, comparing the aBCT with the dBCT, defining based thereon whether there is a need for heating or cooling and emitting a control signal controlling heat transfer properties of said heat exchanger based on the aBCT/dBCT difference and on said HTD.

The control of the heat exchange properties of said heat exchanger may involve change of the heat transfer properties between the heat exchanger and the body surface which may be achieved, for example, by changing the heat conductance parameters between the body's surface and the skin, e.g. by pumping or removing air into or from air pockets disposed between heat radiating/heat absorbing members within the heat exchanger and the skin; or preferably, by changing the temperature of the heat exchanger, which may either be a reduction in the extent of heating or cooling, halting the heating or cooling operation, or reversing the heating or cooling operation into cooling or heating, respectively. In reversing, the heat exchanger acting first as a heat source will be switched to become a heat sink, or vice versa, thus reversing the direction of heat transfer.

The heat exchanger may, for example, comprise electric heating/cooling devices, e.g. Peltier devices and others. However, in accordance with a preferred, non-limiting, embodiment of the invention, the heat exchanger is of a kind comprising one or more conduits or fluid transfer medium for passing the heat control fluid therethrough, for transferring heat to or absorbing heat from the individual's body surface. The fluid, which is typically, though not exclusively, a liquid, e.g. water. may be driven through the conduits or medium by a pump or any other suitable device therefor. Such fluid thus circulates between the heat exchanger and a heat and/or cold source. The heat exchanger is typically flexible to allow it intimate contact with a body surface for efficient heat transfer therewith.

In addition to the above noted measuring devices (the BCT sensing device and the device for measuring a parameter indicative of said HTD), the system may further comprise one or more devices for measuring temperature of the circulating fluid and for emitting data signal relating thereto to the controller. At times, where the system comprises two or more such devices, at least one of which may serve as an inlet temperature sensing device for measuring temperature of the fluid as it enters the at least one conduit or fluid transfer medium, and at least one other may serve as an outlet temperature sensing device for measuring temperature of the fluid as it exits the at least one conduit or fluid transfer medium. The temperature drop ($\Delta T$) between the garment's inlet and the outlet is a very good indicator of said HTD, since this information, together with information on the fluid's flow rate, permits an accurate calculation of the heat transfer between the heat exchanger and the body, which depends on said HTD. Thus, in accordance with a preferred embodiment said $\Delta T$ and the fluid flowrate are used as an HTD-indicating parameter.

The heat exchanger of the invention is typically a garment which is worn over a portion of the individual's body. Typically, the garment may be designed so as to cover at least about 30%, preferably at least about 40% of the body's surface. In this way, the system of the invention effectively stabilizes an individual's body temperature, at a desired body core temperature, within a minimal tolerance. Such a garment may have different forms depending on its intended use. For example, the garment may be designed for use by individuals performing hard labor under extreme hot conditions, for the purpose of cooling their body. For such a purpose the garment has to be relatively flexible so as to limit, as little as possible, the free movement of the individual. By another example, the garment may be designed for medical use, either for the purpose of reducing core temperature of individuals having a disease with a very high fever, for the purpose of increasing core body temperature of hypothermic individuals or for both. A currently preferred embodiment of the invention is the application of the system for control of body temperature of patients during or after general anesthesia. For this purpose the heat exchanger, typically in the form of a garment, may have a variety of openings permitting access for the performance of various surgical procedures, for parental administration of drugs or fluids or for drainage of body fluids, (e.g. excretions or blood).

One example of the use of the system and method of the invention in accordance with the above referred embodiment, is in open heart surgery. Open heart surgery typically involves cooling of the body temperature to about 32° C. During such surgery the heart's activity is temporarily arrested and the blood is circulated through an artificial heart-lung apparatus. Following such surgery, there is a need to increase the body temperature to normal temperature as rapidly as possible, since maintaining such a core body temperature for prolonged time periods may be damaging, at times even life threatening. Today's medical practice involves, towards the end of the surgery, heating of the blood as it circulates through the artificial heart-lung apparatus. However, this heating practice has proven insufficient, as the body's core is not sufficiently heated in this way, and once the blood is disconnected from this apparatus and allowed to recirculate through the reactivated heart, the blood temperature immediately drops. Heating in such procedures is typically performed today by the use of heated blankets, blowing of hot air on the individual, etc. Overall, the methods available today do not allow an efficient monitoring and control of body core temperature. In accordance with the invention, the body core temperature may be controllably cooled during the initial phases of the surgery, then maintained at about 32° C. while applying heating or cooling as needed, and then eventually controllably heated at the end of the surgery to reach normal body temperature.

Generally, the system and method of the invention may be used in control of patient's body temperature during the perioperative period in a wide range of different surgeries.

As will no doubt be appreciated, a heat exchanger in the form of a garment may typically be designed to have various forms and sizes, to meet specifications of individuals of various ages, weights, agendas, etc., or to meet specific requirements of a specific medical procedure.

In addition to use for humans, particularly in human medicine, the method and system of the invention may also find a wide range of applications in veterinary medicine. The same problems of resuming normal body temperature, as well as a controlled cooling during surgery, are also encountered in veterinary medicine. As will be appreciated, the heat exchanger, typically in the form of a pad, a blanket or garment, may be designed to have different shapes, depending on the type of animal, the type of surgery, etc.

A system of the invention for use in the operation room, may typically be designed for exchange of data with other instruments present in the operation room, e.g. import of data relating to blood temperature from heart-lung apparatus, import of data relating to heartbeat or blood pressure from respective measuring devices, etc.

The sensing device for measuring a skin parameter indicative of said HTD (hereinafter referred to at times as "HTD device "), may, in accordance with the one embodiment, include a device for measuring a temperature at a skin portion proximal to a skin portion on which the heat exchanger is applied. The HTD may then be determined, for example, by either one or both of (i) determining the rate of temperature change at said skin portion following heating or cooling of adjacent skin portions by the heat exchanger, or (ii) by assessing the rate of change of temperature difference between the skin portion and the core during heating or cooling of the body.

Said HTD device may, in accordance with another embodiment of the invention, consist of the aforementioned at least two sensing devices for measuring temperature of the fluid as it enters the at least one conduit in the heat exchanger and the temperature as it exits from the at least one conduit. The controller, thus receiving at least two data signals relating to the measured temperature, then calculates said HTD based on the inlets or outlet temperature differential and on the fluid flow rate, which is either determined by the controls or measured by an appropriate measuring device.

In accordance with other embodiments, said HTD device is adapted for measuring a parameter indicative of said HTD, which parameter may be one of a variety of skin and peripheral blood flow parameters. These may be determined by many techniques, e.g. by echo doppler signal techniques, skin conductance, peripheral blood pressure, skin temperature, skin color, etc.

One major feature of the invention relates to the measurements of said heat transfer dynamics (HTD), and taking the heat transfer dynamics into consideration in the heat control regime of the individual. Specifically. when the HTD parameters point to the occurrence of vasoconstriction, any applied cooling should be temporarily halted or reduced. At times, it is advantageous also to reverse the heat transfer mode, temporarily heat in a cooling mode. This means that a cooling mode will involve occasional heat pulses timed and patterned according to said HTD.

The system may have a user interface permitting a user to enter a dBCT, namely a temperature set point of the system. The user interface may further comprise control means allowing selective operation of the system in either an automatic mode, namely in a mode permitting both cooling or heating depending on the direction or deviation of the aBCT from the dBCT. In addition, the control means may also typically allow to select a heat only mode or a cool only mode.

Typically, the heating will be limited so that the temperature at the surface of the heat exchanger which is in touch with the body surface, will not exceed maximum temperature, e.g. a temperature of about 40° C. and not to fall below a minimum temperature, e.g. about 15° C.

In order to be effective in cooling or heating, the heat exchanger, typically in the form of a garment, has to be fitted onto the individual's skin. At times, there is a need to wear such a garment for a prolonged period of time, and this may give rise to a risk of pressure wounds. In order to circumvent this problem in accordance with one embodiment of the invention, the heat exchanger has two or more individually flow-controlled flow sub-systems, and these sub-systems may then be used intermittently, namely, one system being inflated with fluid and used, while the other being deflated and thus not exerting pressure on the skin; and vice versa. In accordance with another embodiment, the fluid transfer to the garment is temporarily halted for periods of several seconds to minutes in order to reduce the pressure onto the skin thus reducing currents of pressure.

In accordance with one embodiment of the invention, the system comprises an electric in-line fluid heating/cooling unit and the circulation fluid is directed to flow through said unit for heating or cooling. Heating or cooling of the fluid in such a unit may also be achieved by means of an auxiliary circulatory heat transfer fluid through the intermediary of a heat exchanger within said unit. In accordance with another embodiment, the system comprises at least one cold fluid reservoir and at least one hot fluid reservoir and comprises a fluid flow control system for selectably drawing fluid from these reservoirs. One advantage of having independent hot and cold fluid reservoirs,. is that the switching between heating and cooling modes can be rapid.

In a system comprising independent hot fluid and cold fluid reservoirs, the flow control system is preferably adapted to permit return fluid to flow back into the reservoir from which it was drawn. It is preferred that during switching from a cold to hot fluid or vice versa, the original fluid will flow initially to the reservoir from which it was drawn, and only after the warm fluid has been exploited will the returned fluid be directed to the other reservoir. Otherwise, the cold reservoir may be heated or the hot reservoir cooled. This may be achieved by having a temperature sensing device measuring the temperature of the fluid flowing out of the heat exchanger and only when the device measures an abrupt temperature change, will the flow control system begin to direct the fluid to the new reservoir.

In order to understand the invention and to see how it may be carried out in practice, a preferred embodiment will now be described by way of a non-limiting example only, with occasional reference to the annexed drawings:

BRIEF DESCRIPTION OF THE DRAWINGS

(FIG. 9B is continuum of FIG. 9A).

DETAILED DESCRIPTION OF PREFERRED EMBODIMENTS

Figure 1A:
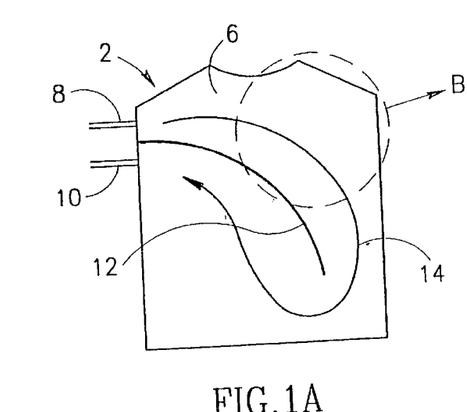
FIG. 1A is a garment in accordance with an embodiment of the invention.
Figure 1B:
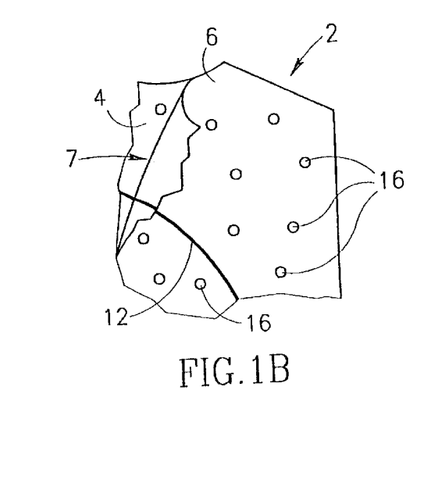
FIG. 1B is an enlargement of the region marked "B" in FIG. 1A with the two external layers being partially separated for illustrative purposes.

A top view of a garment 2 in accordance with one embodiment of the invention shown in an open layout can be seen in FIG. 1. Garment 2 is designed for fitting over a person's torso. Garment 2, as can specifically be seen in FIG. 1B, is formed with two external layers 4 and 6 defining between them a fluid passage space 7. The garment is provided with a fluid inlet 8 and a fluid outlet 10 for respective fluid ingress and egress into and out of the fluid passage space. The garment is provided with a partition 12 which defines a fluid flow-path which is represented schematically by arrowed line 14. This fluid is typically water but may also be any other suitable liquid, e.g. alcohol, oil, etc., and may also, in other embodiments be a gas, e.g. air.

As can further be seen in FIG. 1B, the garment is formed with a matrix of welded points 16 where the two external layers 4 and 6 of the garment 2 are welded one to another. In use the pressure of the fluid forces the two layers away from one another filling fluid in the space between the welded points. The welded points ensure the structural integrity of the two layers and further ensure some resistance to fluid flow and consequently substantially even distribution of fluid flow through the garment's entire fluid passage space 7. As will no doubt be appreciated, the internal structure of the garment is but an example. By other embodiments the garment may comprise two external layers sandwiching a porous matrix between them; may comprise tubes or other conduits embedded or defined therein by welded lines; etc.

Figure 2:
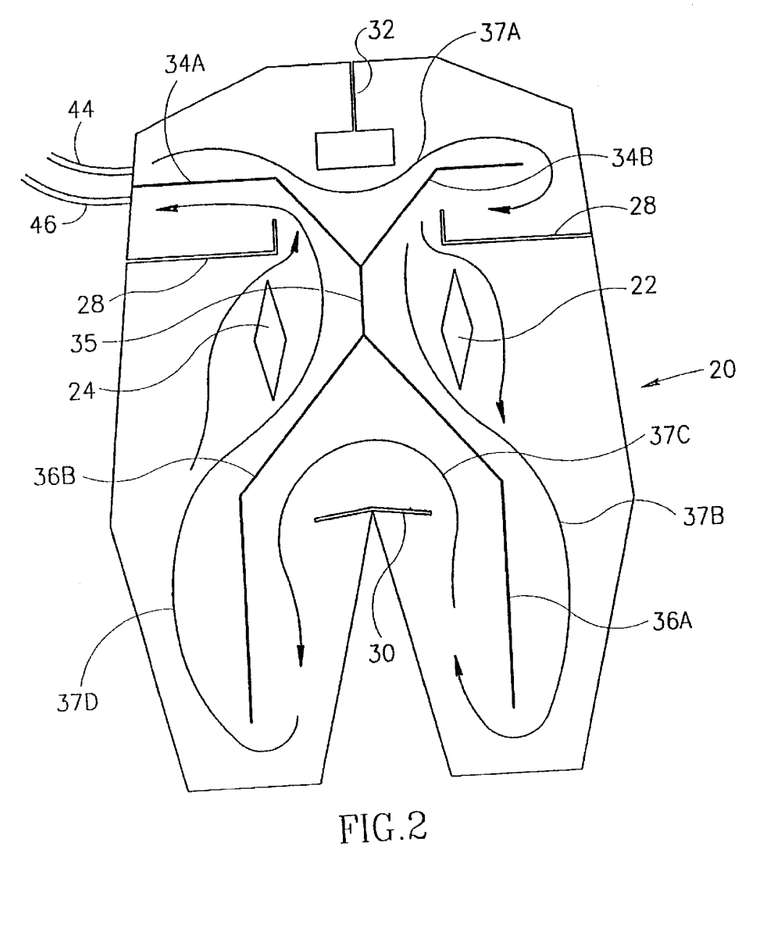
FIG. 2 illustrates a top view of a laid-open garment, for use in the system in accordance with an embodiment of the invention.
Figure 3:
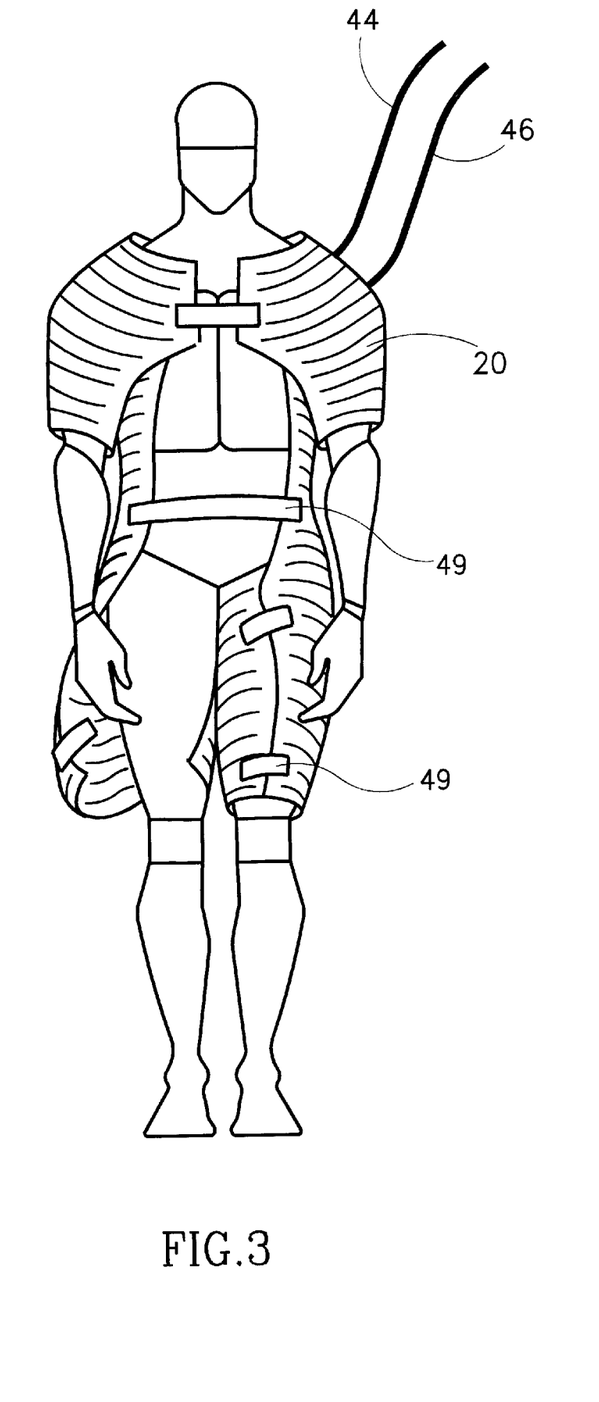
FIG. 3 is a schematic illustration of the garment of FIG. 1, applied to a patient.

A top view of a garment in accordance with another embodiment shown in open layout, and generally designated 20, can be seen in FIG. 2. The garment 20 has openings 22 and 24, which allow, when the garment is fitted on a person, access to the underlying skin portion, e.g. for skin temperature measurements, for injection, etc. Rather than openings 22 and 24 the garment may also be provided with flaps serving a similar purpose. The garment is provided with several cuts 28, 30 and 32 for fitting of the garment on the individual, as can be seen in FIG. 3. The garment which may have a similar internal structure to that shown in FIG. 1B, is formed with weld lines 34A, 34B, 35, 36A and 36B which together define a fluid flow path as represented by arrowed lines 37A, 37B, 37C and 37D extending between the fluid inlet 44 and outlet 46. In this case, the garment is structured such that the chest and abdominal portion of the individual are left open, thus rendering this garment suitable for chest and abdominal surgery. For other surgical applications, the garment may assume a variety of different shapes. In addition, the garment may also be provided in various sizes for fitting individuals of different weights, gender, age, etc.

The garment may be made of a variety of different materials including fabrics, plastic materials, etc. The garment should preferably be flexible and elastic to allow it to fit over an individual's body. The outer layer of the fabric may be coated with a heat insulating material, to prevent heat transfer to the external environment. In addition, the garment may have an internal soft lining such as felt, in order to avoid occurrence of pressure wounds.

Furthermore, as will be explained with reference to FIG. 5, the garment may be provided with an internal fluid absorbent layer.

The garment may be made for multiple use, or occasionally may be made disposable. The garment made for multiple use should be made of such materials as to allow its sterilization by any one of a plurality of sterilization means known per se.

Figure 4:
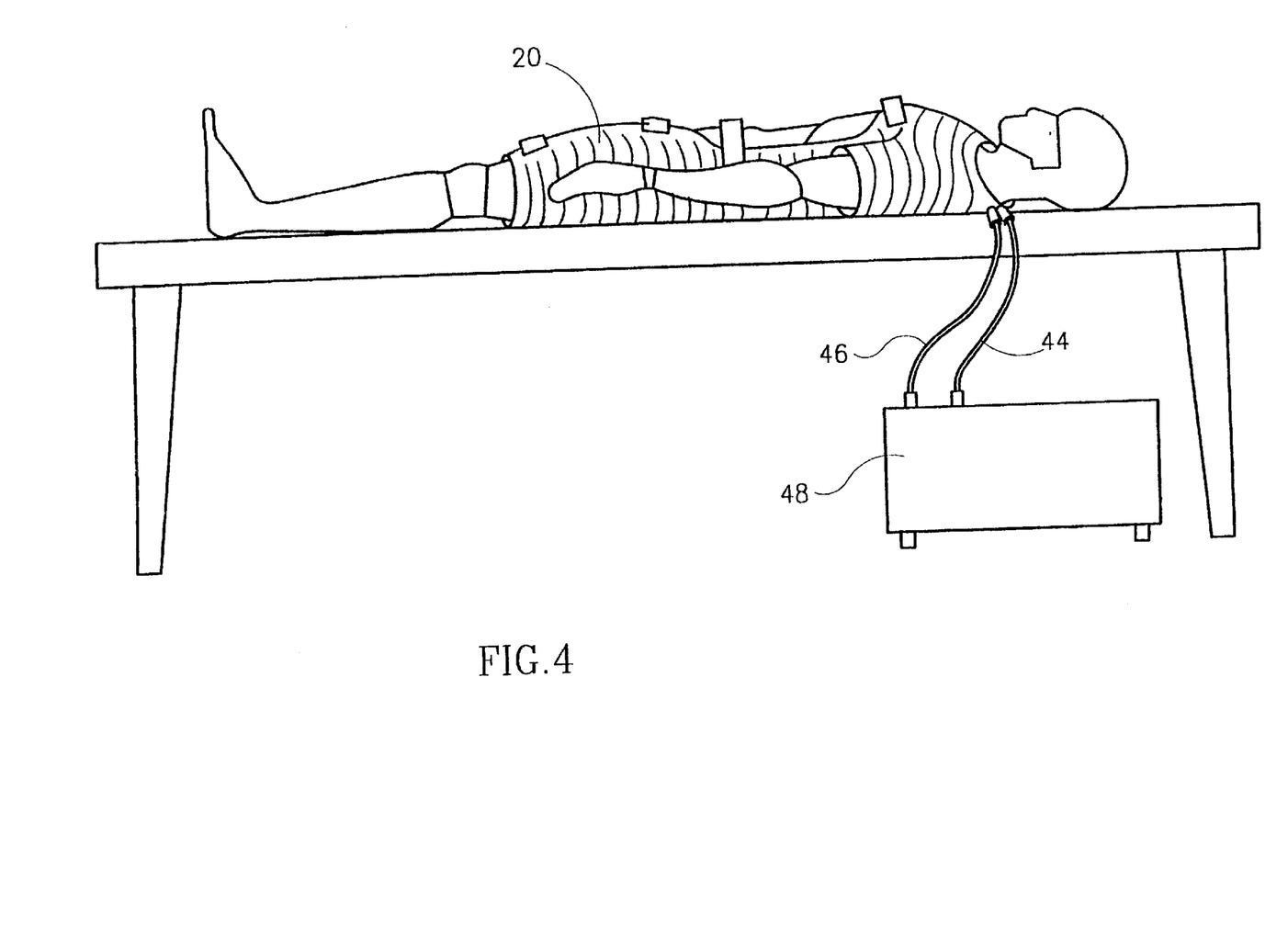
FIG. 4 is a side elevation of the patient with the garment of FIG. 3.

As can be seen in FIGS. 2–4, fluid inlet/outlet tubings 44, 46 are connectable to a liquid temperature control unit 48 (seen in FIG. 4).

In order to allow easy fixing and removal of the garment, it is typically provided with detachable fixing means, such as a hook and pile (e.g. Velcro™) type attachment members 50.

Figure 5:
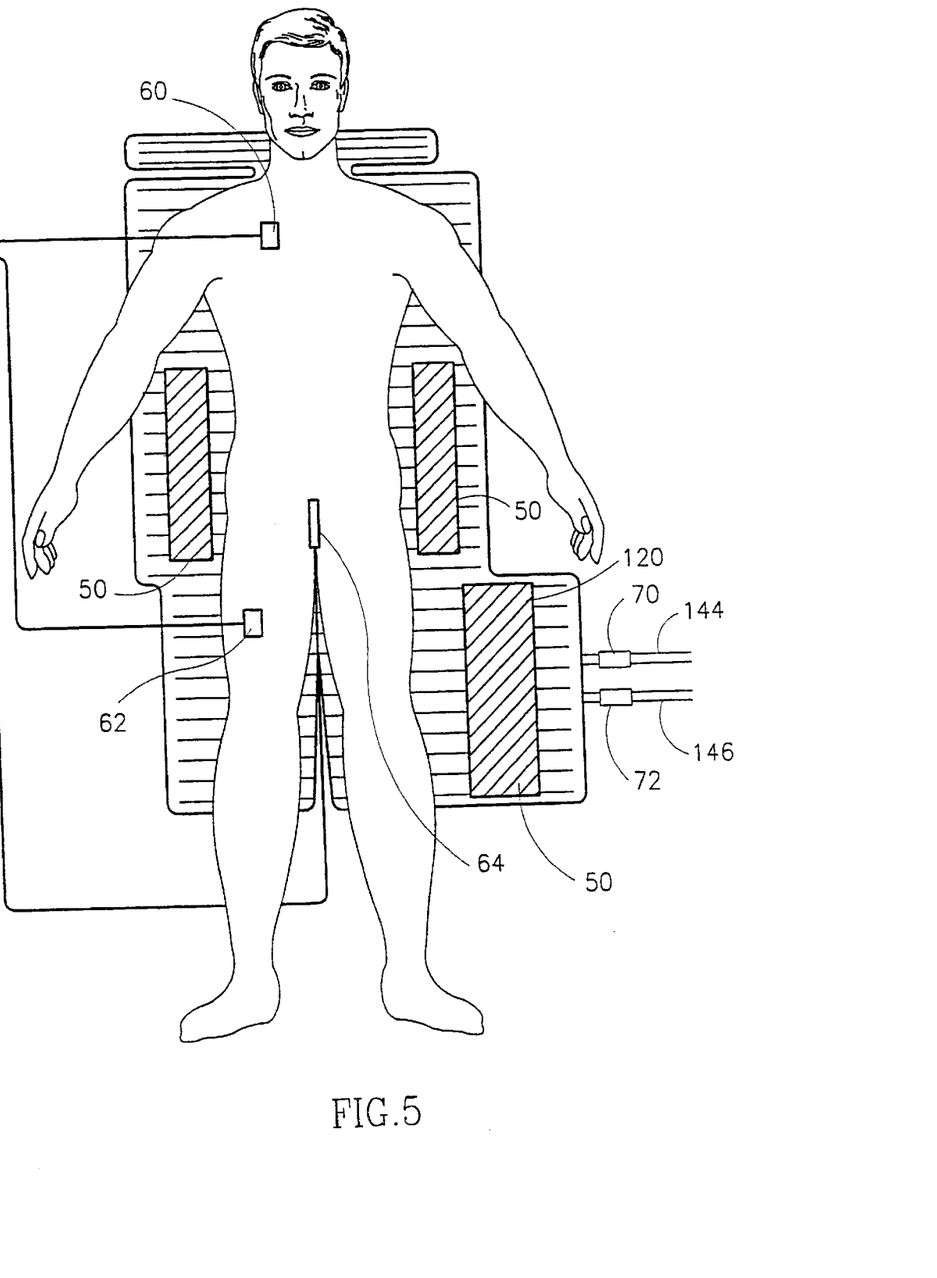
FIG. 5 shows a garment in accordance with another embodiment of the invention, in an open state with the patient lying thereon provided with an adhesive matrix.

FIG. 5 is a planar view of a garment 120 in accordance with another embodiment of the invention, still in an open position, prior to fixing it over the patient's body. In this figure, like reference numerals to those of FIGS. 2–4 were used, with a "100" index (namely with a "1" prefix) and the reader is referred to the description relating to FIGS. 2–4 for their explanation. Further seen in FIG. 5, are matrices 50 which are made of an absorbent material. Typically, such a matrix has a fluid permeable layer, and a hygroscopic material capable of absorbing liquids and retaining them within. Such matrices of liquid absorbent properties, are readily known in the art, and a detailed description of their structure goes beyond the present writing.

Also seen in FIG. 5, are skin-temperature sensing probes 60 and 62 and a rectal temperature probe 64 for measuring core temperature. In addition, other types of temperature measuring devices may be provided, e.g. an intra-ear temperature measuring device, an infrared sensor for measuring skin temperature, an oral temperature measuring device for measuring core temperature, etc. As explained above, the skin temperature is measured, in accordance with one embodiment of the invention, in order to determine the heat transfer dynamics (HTD) of the skin. For the same purpose, as an alternative to measurement of skin temperature, other parameters may be measured which include skin color, skin conductance, peripheral blood pressure, temperature drop of the heating or cooling fluid (as will also be outlined below), as well as any other parameters which can give an indication of occurrence of vasoconstriction or vasodilatation.

In addition, advantageously, temperature sensing devices 70 and 72 for measuring inlet and outlet fluid temperature may also be provided. Such information may also be utilized for the rate of heat transfer between the heat exchanger, namely the garment, and the skin in order to assess the HTD.

Figure 6:
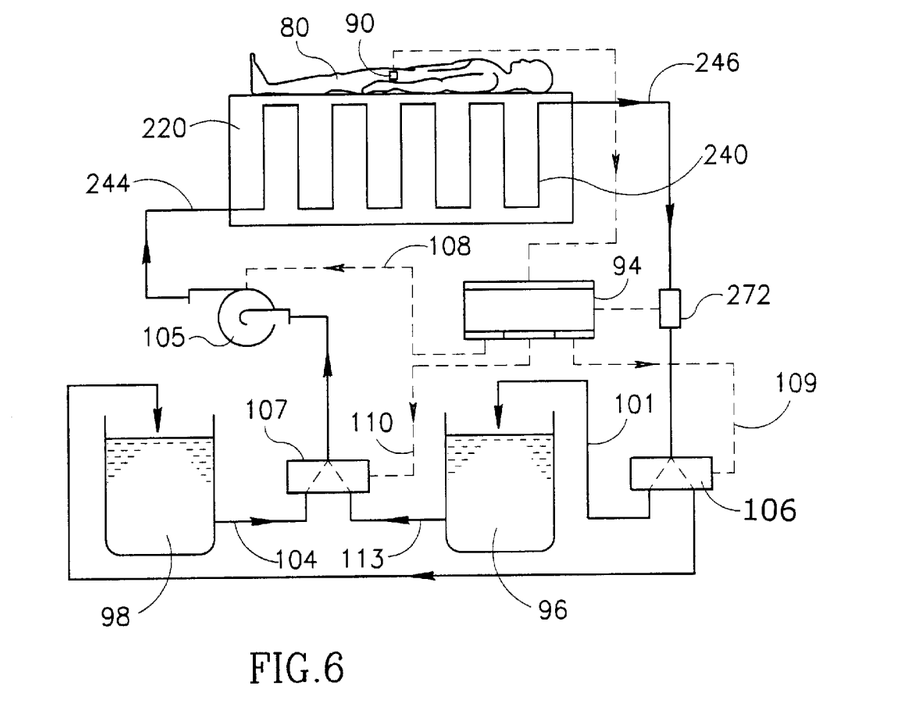
FIG. 6 is a schematic general illustration of a system in accordance with the invention.
Figure 7:
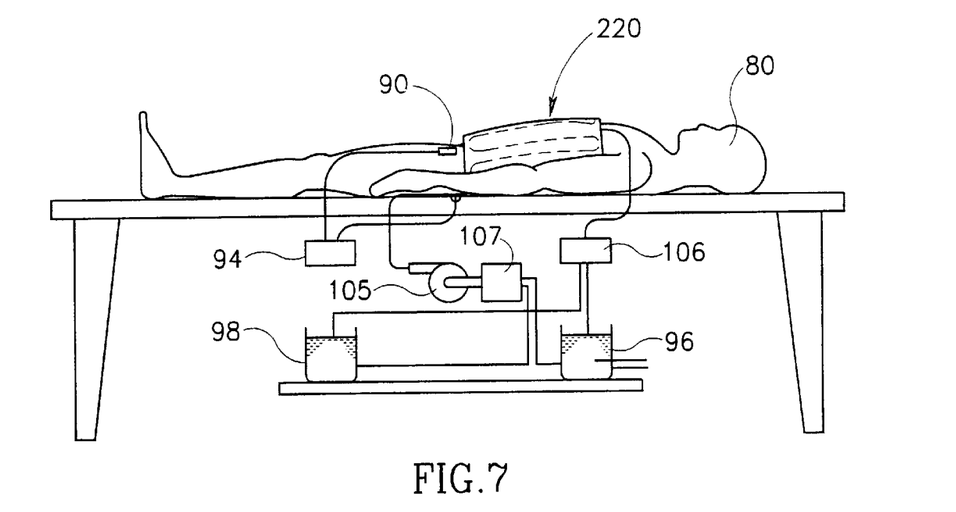
FIG. 7 is a schematic side elevation of the system of FIG. 6.

A schematic representation of the system in accordance with another embodiment of the invention can be seen in FIGS. 6 and 7. A patient 80 as shown herein is provided with a garment 220 (shown schematically as a rectangle in FIG. 5). In FIGS. 6 and 7, the same reference numerals to those used before are used, where applicable, with "200" index. Garment 220 is provided with a fluid inlet 244 and outlet 246 and with a continuous fluid conduit or a continuous porous space 240 between them, embedded in garment 220. A plurality of sensing devices shown herein schematically as component 90, transmit data signals reflecting the patient's physiological parameters, are transmitted to controller 94.

The system of this embodiment is adapted for both heating or cooling the patient. By one embodiment, hot fluid and cold fluid are provided from respective, independent hot and cold fluid reservoirs 96 and 98. Each of the reservoirs has respective fluid inlets 101, 102 and respective fluid outlets 103, 104. The system is provided with a pump 105 for propelling fluid within the system.

The system is provided with two flow control valves 106 and 107, for selectively transferring return fluid to or drawing fluid from one of the two reservoirs. Pump 105 and flow control valves 106 and 107, are electrically operated by controller 94 through command lines, 108, 109 and 110, respectively.

When switching from a heating mode to a cooling mode or vice versa, the flow control valves are switched accordingly. In accordance with one embodiment of the invention, the fluid outlet 246 is provided with a heat sensor 272 which allows switching of the returning fluid from one reservoir to another only upon sensing an abrupt temperature change by sensing device 272, which then transmits a data signal to controller 94 which in turn causes flow control valve to switch. The arrangement is such that the first flow control valve to be switched will be valve 107 and if, for example, the switch was from a cold fluid to a hot fluid, valve 106 will continue to direct the return fluid into reservoir 102 and only upon registering an abrupt temperature drop by sensor device 272 will be return fluid be channeled to reservoir 96.

Figure 8:
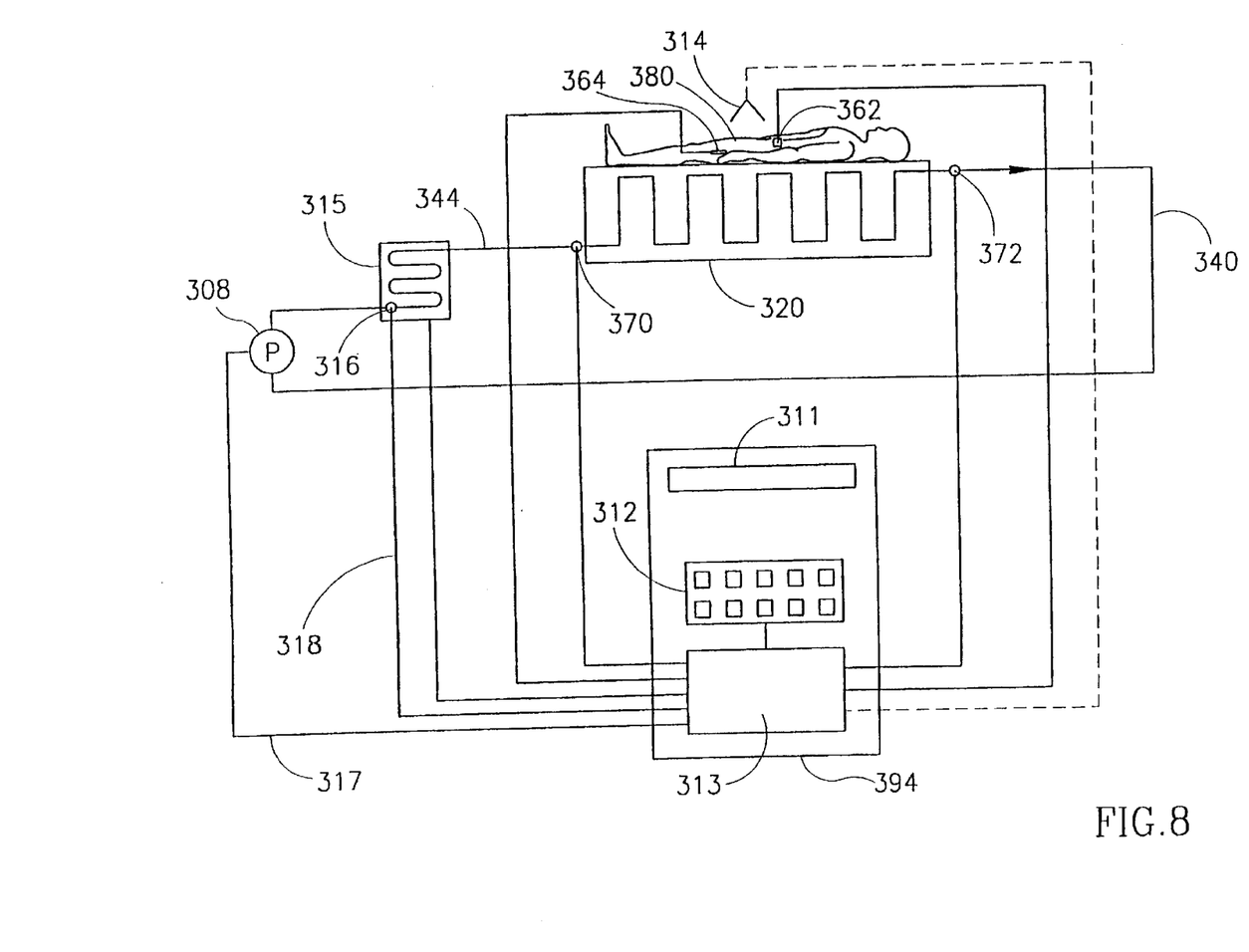
FIG. 8 is a principal schematic illustration of a system in accordance with another embodiment of the invention.

In other embodiments, such as that shown in FIG. 8, heating and cooling of the working fluid is carried out "on-line" by a heat pump operating as heater/cooler unit. Such a unit which may, for example, be provided with Peltier effect heat pumps, may easily be controlled to either heat or cool the fluid passing therethrough.

A schematic description of a system in accordance with an embodiment of the invention can be seen in FIG. 8. Here again, like reference to those used previously in the description, with a "300"index were used and the reader is referred to the previous description for explanation of their function. Controller 394 is provided with a display 311 to display the registered parameters, e.g. measured core temperature, the measured skin temperature, the desired core temperature, flow rate, fluid temperature, etc. In addition, controller is provided with a control panel 312 and a processor 313. The processor 313 receives data signals from all sensing devices (core temperature measuring device 364, skin temperature measuring device 362, an optional infrared-skin-temperature measuring device 314, and others). In addition, the processor also receives temperature data from inlet and outlet fluid temperature sensing devices 370 and 372 and temperature registered in heating/cooling device 315 by means of a sensor 316. Device 315 may for example be a Peltier effect heat pump, as known per se. In addition, the controller controls the flow rate of pump 308 via command line 317 and controls the temperature of device 315 through line 318.

On the basis of the various data signals registered by the processor, and implementing various algorithms designed in accordance with the general teaching of the invention, e.g. that exemplified below, the flow rate of the fluid and/or the temperature of the fluid may be controlled. Various servo loops may be implemented through processor 313 for proper control of the various parameters.

FIG. 8 shows an algorithm, by way of blocked diagram, of the various computational steps of the algorithm operating in a processor in accordance with the embodiment of the invention. Contrary to previous figures, the reference numerals used in this figure have no bearing to previously used reference numerals.

Figure 9A:
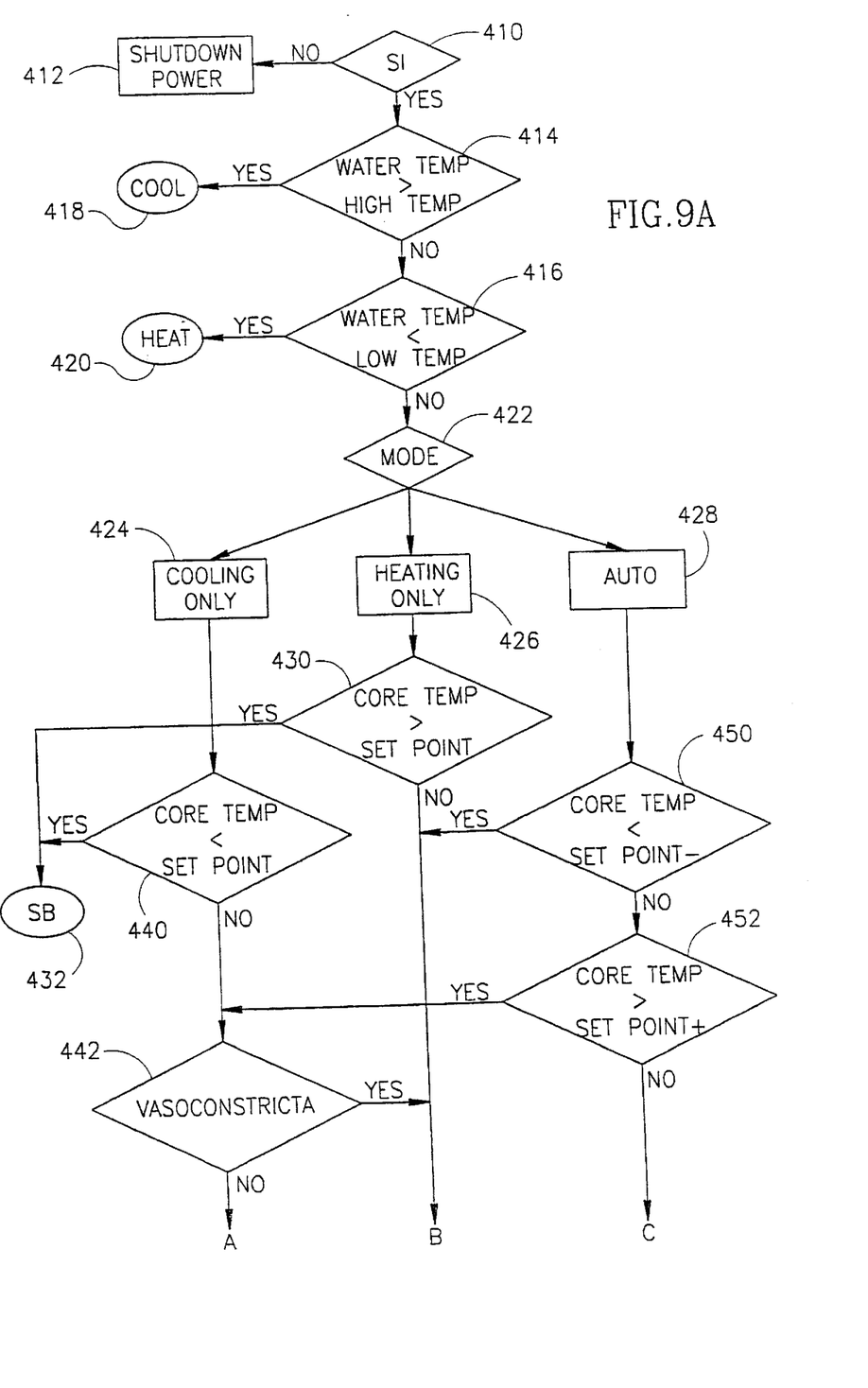
FIGS. 9A and 9B show a schematic block diagram of the algorithm operating in the system in accordance with one embodiment of the invention.

In a first decision step 410 the system is initiated and integrity is checked. If the system detects a fault, in any of its components, a system shut down sequence 412 is initiated. In the initiation step, the various operational modes are set. These may be automatic, heating only or cooling only modes.

Other parameters which may be set by the user are minimal and maximal permitted temperature of the heat transfer liquid, typically water to prevent tissue damage as well as discomfort to the patient, particularly when not under general anesthesia.

In the next two decision making steps 414 and 416, the actual water temperature (designated in the figure as "WATER TEMP") is compared to the maximally allowed water temperature ("HIGH TEMP") and to the minimal allowed water temperature ("LOW TEMP"). In case in step 414 the water temperature is found to be above the HIGH TEMP limit, a cooling sequence 418 is initiated, and in the case the water is found in step 416 to be too cold, the heating sequence 420 is initiated.

At the next decision step 422, a mode is selected based on the user's input, between cooling only mode, heating only mode or automatic mode, designated 424, 426 and 428, respectively.

In the first decision step 430 of the heating mode, the body core temperature ("CORE TEMP") is compared to the desired body core temperature ("SETPOINT"). Where the body core temperature is found to be above the set point, the system is primed to enter to a standby mode 432, namely the heating function is terminated. During the standby mode, the core temperature is continuously measured and compared to the set point.

When the core temperature is determined to be below the set point, the water temperature is compared to the high temperature at 434 and if the water temperature is below the high temp, the heat mode 420 is initiated. If the water temperature is found to be above high temp, the system is primed again to enter into a standby mode 432.

Figure 9B:
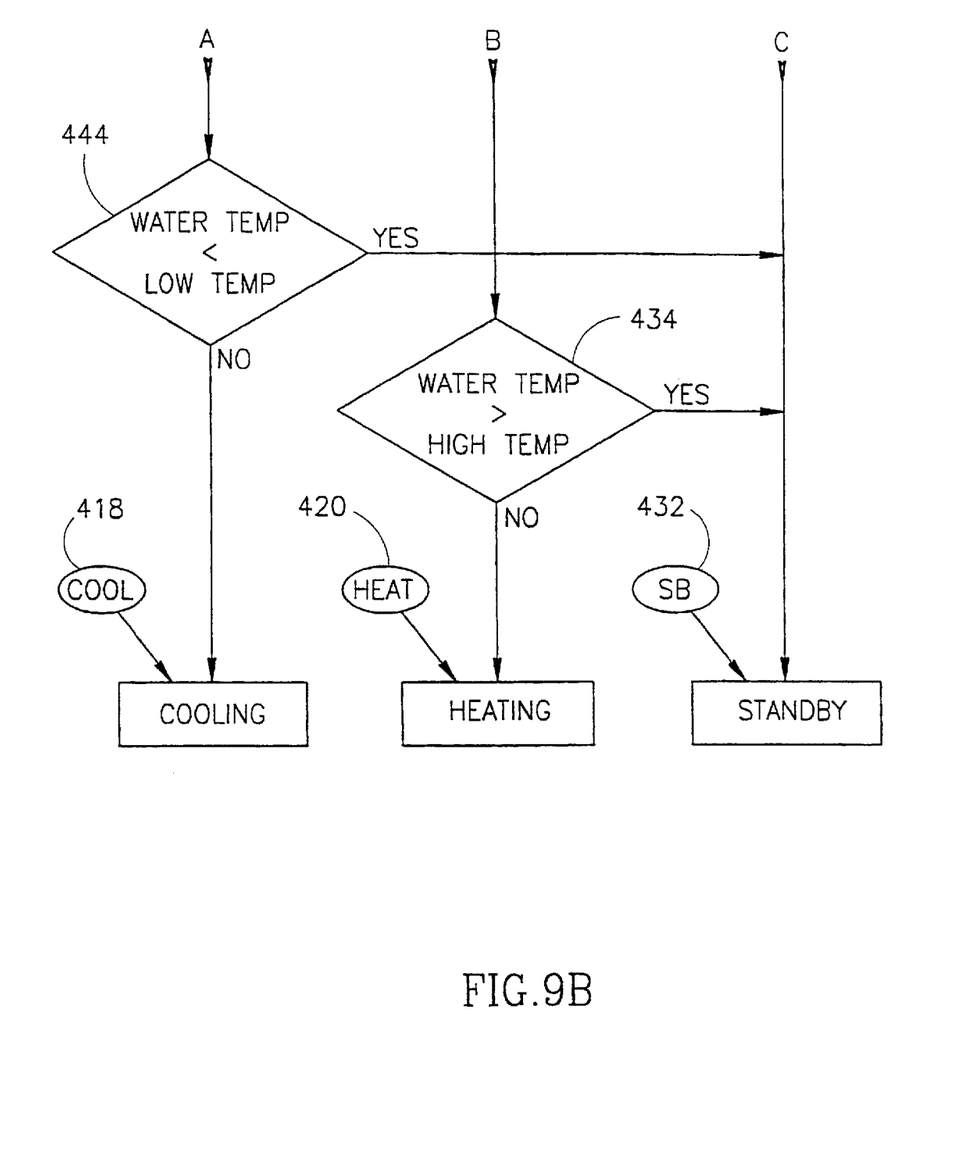

In the first decision making step 440 of the cooling mode 424, the body core temperature is compared to the set point and if found to be below the set point, the system is primed into standby mode 432. If the core temperature is below the set point, the system determines whether vasoconstriction of the skin has occurred 442. If there is no vasoconstriction, the cooling mode progresses into a next decision making step 444 where the water temperature is compared to the minimal allowed temperature. If water temperature is less than LOW TEMP then the system is primed to enter into a standby mode 432, and if above, the cooling sequence 418 is initiated.

In step 442, if vasoconstriction is found to have occurred (i.e. low heat conductance between the core and the periphery) notwithstanding the fact that there is a cooling mode, a heating sequence is initiated. When vasoconstriction is determined to have ceased, the cooling sequence is reinstated.

In a first decision making step 450, of the automatic mode 428, the core temperature is compared to the set point. if found to be below the set point, the system enters the heating mode 426. If the core temperature is found to be below the set point, the sequence proceeds to the next decision making step 452 and there, if the core temperature is found to be above the set point, the cooling sequence 424 is initiated. If the core temperature is found to be below the set point, the system is shifted towards the standby mode.

In the algorithm described above, the only parameter controlled is the water temperature. It should be appreciated, that in other embodiments, parameters such as flow rate of the heat transfer fluid may also be controlled. In addition, various other parameters, such as blood temperature, based on data imported from artificial heart-lung apparatus, may also be factored in the system's output.

As will be appreciated, the determination of the occurrence of vasoconstriction may be based on a variety of parameters, as noted above in the description, making use of data received from one or more of the above described sensing devices.

What is claimed is:

1. A system for controlling an individual's body core temperature (BCT) comprising:
   a heat exchanger for transferring heat to or removing heat from portions of the individual's body surface;
   at least one BCT-sensing device for measuring the individual's actual BCT (aBCT) and emitting an aBCT data signal;
   at least one sensing device for measuring a parameter indicative of the heat transfer dynamics (HTD) between the body surface and the body's core, and emitting an HTD data signal; and
   a control module for receiving data signal from measuring devices, comprising the aBCT data signal and the HTD data signal, and for emitting a control signal for controlling heat exchange properties of said heat exchanger as a function of the data signals and a desired body core temperature (dBCT).

2. A system according to claim 1, wherein said heat exchanger comprises one or more conduits for passing heat control fluid therethrough, for transferring heat to or absorbing heat from the individual's body surface.

3. A system according to claim 2, wherein the heat exchanger is coupled to a device for circulating the heat control fluid through the conduits.

4. A system according to claim 2, comprising one or more devices for measuring temperature of the circulating fluid and for emitting data signal relating thereto to the controller.

5. A system according to claim 2, wherein said fluid is a liquid.

6. A system according to claim 1, wherein said heat exchanger is in a form of a garment to be worn over a portion of the body.

7. A system according to claim 1, for use in control of a patient's body temperature during or after general anesthesia or in a perioperative period.

8. A system according to claim 7, wherein said heat exchanger is in a form of a garment to be worn over a portion of the body.

9. A system according to claim 8, wherein said garment has openings permitting access for surgical procedures, for parental administration or for drainage of fluids.

10. A system according to claim 7, wherein at least a portion of the garment is fitted with a removable and flexible liquid absorbent matrix.

11. A system according to claim 1, wherein said sensing device for measuring a parameter indicative of said HTD includes a device for measuring temperature at a skin portion proximal to a skin portion on which the heat exchanger is applied, and determination of the HTD is based on assessing the rate of temperature change.

12. A system according to claim 1, wherein said sensing device for measuring said skin parameter includes a device for measuring temperature at a skin portion proximal to a skin portion on which the heat exchanger is applied, and determination of the HTD is based on determining the rate of change of temperature difference between said skin portion and the body core.

13. A system according to claim 4, comprising at least one inlet temperature sensing device for measuring temperature of the fluid as it enters the at least one conduit, and at least one outlet temperature sensing device for measuring temperature of the fluid as it exits the at least one conduit, these sensing devices being coupled with the controller and emitting respective data signals thereto; the controller calculating said HTD based on the inlet/outlet temperature differential and on the fluid flow rate.

14. A system according to claim 1, wherein said surface parameter comprises a parameter selected from the group consisting of body's surface temperature, skin color, peripheral skin blood pressure, electrical skin, conductance of the skin, echo doppler signal.

15. A system according to claim 1, wherein during heating or cooling, the heating or cooling operation, respectively, is occasionally temporarily halted or reversed to respective cooling or heating.

16. A system according to claim 15, wherein halting or reversing of heating or cooling is automatically performed when determined HTD indicates reduction in heat transfer properties between the periphery and the body's core, signifying the occurrence of vasoconstriction.

17. A system according to claim 1, wherein the controller has a cooling operational mode, a heating operational mode and an automatic operational mode for heating or cooling depending on the difference between core temperature and desired core temperature.

18. A system according to claim 1, comprising a user control interface permitting a user to set the dBCT, or set the system to operate in either of a cooling operational mode, a heating operational mode or an automatic operational mode.

19. A system according to claim 1, wherein the temperature of the heat exchanger is maintained between a minimum and a maximum temperature to avoid tissue damage in view of exposure to access heating or cooling.

20. A system according to claim 1, wherein the heat exchanger is formed with at least two individually flow-controlled flow sub-systems.

21. A system according to claim 2, comprising at least one electric fluid heating/cooling unit and the fluid is directed to flow through said unit.

22. A system according to claim 2, comprising at least one cold fluid reservoir and at least one hot fluid reservoir and a fluid flow control system for selectively drawing fluid from these reservoirs.

23. A system according to claim 22, wherein the fluid flow control system permits returned fluid to flow back into the reservoir from which it was drawn.

24. A system according to claim 22, comprising at least one temperature sensing device measuring temperature of the fluid flowing out of said heat exchanger, and upon change of drawn fluid from one reservoir to another the fluid flow control system initially directs the return fluid to said one reservoir and when said sensing device senses a substantial temperature change it directs the return fluid to said other reservoir.

25. A method for controlling internal body temperature of an individual, comprising the following steps:

(a) defining a desired body core temperature (dBCT);

(b) providing a heat exchanger in contact with at least a portion of the individual's external body surface, for heat transfer to or heat removal from the body portion;

(c) continuously measuring parameters including at least the actual body core temperature (aBCT) and a parameter indicative of the heat transfer dynamics (HTD) between the body's surface and the body's core;

(d) in a processor, receiving data signals corresponding with the measured parameters, comparing the aBCT with the dBCT, defining based thereon whether there is a need for heating or cooling and emitting a control signal controlling heat transfer properties of said heat exchanger based on the aBCT/dBCT difference and on said HTD.

26. A method according to claim 25, wherein the heat transfer to and from the body portion is achieved by transfer of heat control fluid through said heat exchanger.

27. A method according to claim 26, wherein said fluid is a liquid.

28. A method according to claim 25, for controlling of a patient's body temperature during or after general anesthesia.

29. A method according to claim 25, comprising continuously monitoring a temperature at a skin portion proximal to a skin portion in which the heat exchanger is applied, and determining said HTD based on the rate of temperature change at said skin portion.

30. A method according to claim 25, comprising continuously monitoring temperature at a skin portion proximal to a skin portion in which the heat exchanger is applied, and determining said HTD based on determining the rate of change of temperature at a difference between said skin portion and the, body core.

31. A method according to claim 26, comprising continuously monitoring the inlet fluid temperature, namely the temperature of the fluid entering said heat exchanger, and the outlet fluid temperature, namely the temperature of the fluid as it exits from said heat exchanger, and said HTD is calculated based on the inlet/outlet temperature differential and on the fluid flow rate.

32. A method according to claim 25, wherein said parameter indicative of said HTD is selected from the group consisting of body's surface temperature, skin color, peripheral skin blood pressure, electrical skin, conductance of the skin, echo doppler signal.

33. A method according to claim 25, wherein during heating or cooling, the heating or cooling operation, respectively, is occasionally temporarily halted or reversed to respective cooling or heating.

34. A method according to claim 33, wherein the halting or reversing of the heating or cooling, is performed when said parameter is indicative of said HTD, indicates the occurrence of vasoconstriction.

* * * * *

UNITED STATES PATENT AND TRADEMARK OFFICE
CERTIFICATE OF CORRECTION

PATENT NO.   : 6,508,831 B1
DATED        : January 21, 2003
INVENTOR(S)  : Kushnir It is certified that error appears in the above-identified patent and that said Letters Patent is hereby corrected as shown below:

Column 14,
Line 11, after "portion and the" and before "body care", please remove ",".

Signed and Sealed this

Eleventh Day of March, 2003

JAMES E. ROGAN
*Director of the United States Patent and Trademark Office*